United States Patent

Schurr et al.

[11] Patent Number: 5,338,667
[45] Date of Patent: Aug. 16, 1994

[54] MICROBIOLOGICAL PROCESS FOR THE PRODUCTION OF MALONYL-7-AMINO-CEPHALOSPORANIC ACID DERIVATIVES USING SPHINGOMONAS SP. DSM 7007

[75] Inventors: Sabine Schurr, Eimeldingen, Fed. Rep. of Germany; Andreas Tschech, Aarau, Switzerland

[73] Assignee: Lonza Ltd., Gampel/Valais, Switzerland

[21] Appl. No.: 52,623

[22] Filed: Apr. 27, 1993

[30] Foreign Application Priority Data

Apr. 29, 1992 [CH] Switzerland .................. 1381/92

[51] Int. Cl.$^5$ .............. C12P 1/00; C12P 35/00; C12P 35/06; C12N 1/00
[52] U.S. Cl. ........................ 435/47; 435/41; 435/49; 435/822; 435/252.1
[58] Field of Search ............ 435/41, 47, 49, 252.1, 435/822

[56] References Cited

FOREIGN PATENT DOCUMENTS 2258448  8/1975  France .
2434169  3/1980  France .
51-070884  6/1976  Japan .
62-48380  3/1987  Japan .

OTHER PUBLICATIONS

J. Bacteriol., vol. 169, No. 12, (1987), pp. 5815 to 5820.
Jeffery et al., Biochem. J., 81, (1961), pp. 591 to 596.
Bull. Soc. Chem. Belg., 86, (1977), pp. 991 to 1002.

Primary Examiner—David M. Naff
Assistant Examiner—Deborah K. Ware
Attorney, Agent, or Firm—Fisher, Christen & Sabol

[57] ABSTRACT

Disclosed is a microbiological process which utilizes a biologically pure culture of Sphingomonas sp. DSM 7007 in order to produce a malonyl-7-aminocephalosporanic acid derivative product. Furthermore the process uses cephalosporin C derivative as a substrate for the conversion of the cephalosporin C into the product. The process takes place by one time or continuous addition of substrate so that the concentration of cephalosporin C does not exceed 20 percent by weight. Furthermore, the process is performed at a temperature range of 0–60 degrees celsius and a pH range of 5 to 9.

4 Claims, No Drawings

MICROBIOLOGICAL PROCESS FOR THE PRODUCTION OF MALONYL-7-AMINO-CEPHALOSPORANIC ACID DERIVATIVES USING SPHINGOMONAS SP. DSM 7007

BACKGROUND OF THE INVENTION

1. Field Of The Invention

The invention relates to new malonyl-7-aminocephalosporanic acid derivatives of the general formula:

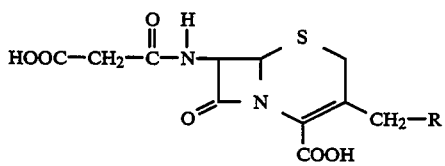

wherein which R means a hydrogen atom, a hydroxyl group or an acetoxy group, a new process for production of such derivatives and salts, which starts from the corresponding cephalosporin C derivatives, and new microorganisms suitable for utilization in such process. The invention also relates to a new microbiological process for the production of 7-aminocephalosporanic acid derivatives which starts from malonyl-7aminocephalosporanic acid derivatives as well as the new use of microorganisms of genus Pseudomonas sp. (DSM 7509).

2. Background Art

Malonyl-7-aminocephalosporanic acid derivatives can be used, for example, as the initial material for the production of 7-aminocephalosporanic acid derivatives, which in turn are important initial compounds for the production of cephalosporin antibiotics [J. Bacteriol., Vol. 169, No. 12, (1987), pages 5815 to 5820]. So far, neither chemical nor microbiological processes for the production of malonyl-7-aminocephalosporanic acid derivatives are known.

For the production of 7-aminocephalosporanic acid, several microbiological processes which start from cephalosporin C are known, such as, the process described in Japanese Published Patent Application No. 62-48380. However, these processes all have the drawback that they are not feasible on an industrial scale.

BROAD DESCRIPTION OF THE INVENTION

An objective of the invention is to provide, with new microorganisms, a new simple and economical microbiological process for the production of new malonyl-7-aminocephalosporanic acid derivatives. Another objective of the invention is to provide with these new derivatives a new microbiological process for the production of 7-aminocephalosporanic acid derivatives.

The objectives of the invention are achieved with the new microorganisms, with the new processes and the new malonyl-7aminocephalosporanic acid derivatives of the invention.

The invention involves microorganisms that are so selected so that they are able to utilize the lactone of the formula:

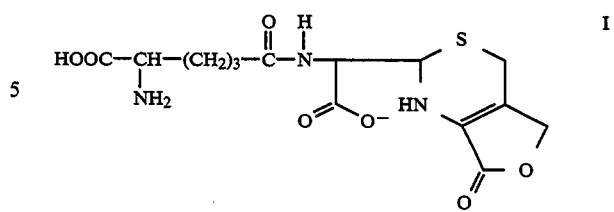

or its soluble salts, as the sole carbon, nitrogen and energy source via a malonyl-lactone of the formula:

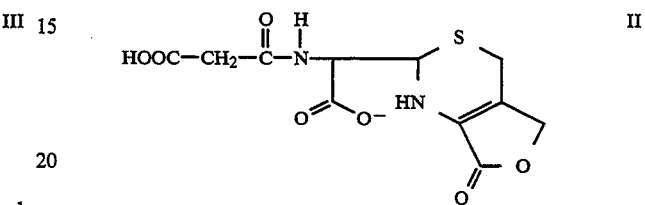

or its soluble salts, and not to catabolize the latter. Preferably the microorganisms are those with the designation Sphingomonas sp. FB1 (DSM 7007) as well as their descendants and mutants.

The invention also involves the microbiological process for the production of malonyl-7-aminocephalosporanic acid derivatives of the general formula:

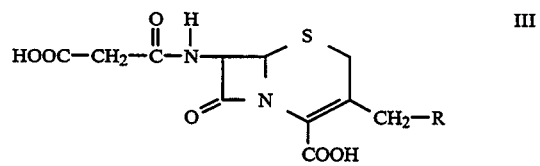

wherein R means a hydrogen atom, a hydroxyl group or an acetoxy group, or their soluble salts. In the process, cephalosporin C derivatives of the general formula:

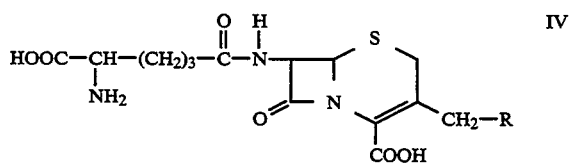

wherein R has the above-mentioned meaning, or their soluble salts, are converted as the substrate by the microorganisms identified just above into the product according to formula III. Preferably the reaction is performed by microorganisms Sphingomonas sp. FB1 (DSM 7007) or their descendants and mutants. Preferably cephalosporin C is used as the substrate. Preferably the reaction takes place by one time or continuous substrate addition so that the substrate concentration in the culture medium does not exceed 20 percent by weight. Preferably the reaction is performed at a temperature of 0° to 60° C. and a pH of 5 to 9.

The invention also includes the malonyl-7-aminocephalosporanic acid derivatives of the general formula:

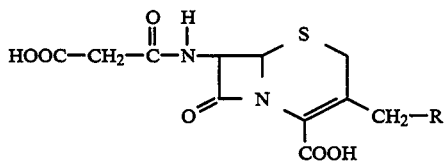

III wherein R means a hydrogen atom, a hydroxyl group or an acetoxy group, or their soluble salts. Preferably such derivative is malonyl-7-aminocephalosporanic acid.

The invention further involves the microbiological process for the production of 7-aminocephalosporanic acid derivatives of the general formula:

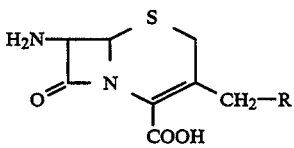

V wherein R has the above-mentioned meaning or their soluble salts. In the process, malonyl-7-aminocephalosporanic acid derivatives of the general formula III or their soluble salts, as the substrate are converted by microorganisms of genus Pseudomonas sp. (DSM 7509) or their descendants and mutants, or with cell-free enzymes from these microorganisms, into the product according to formula V. Preferably malonyl-7-aminocephalosporanic acid is used as the substrate. Preferably the reaction takes place by one-time or continuous substrate addition so that the substrate concentration in the culture medium does not exceed 10 percent by weight. Preferably the reaction is performed at a temperature of 4° to 50° C. and a pH of 4 to 9.

The invention also includes the process of utilizing the microorganisms of genus Pseudomonas sp. (DSM 7509) for the hydrolysis of malonyl-7-aminocephalosporanic acid derivatives of the general formula III or their soluble salts, into 7-aminocephalosporanic acid derivatives of the general formula V. Preferably malonyl-7-aminocephalosporanic acid is hydrolyzed into 7-aminocephalosporanic acid.

DETAILED DESCRIPTION OF THE INVENTION

As used herein, the terms malonyl-7-aminocephalosporanic acid derivatives (formula III), cephalosporin C derivatives (formula IV), malonyl-lactone according to formula II and lactone according to formula I are to be understood as also including the soluble salts, such as, their ammonium or alkali salts, of such compounds.

The microorganisms according to the invention are selected so that they are able to utilize the lactone of the formula:

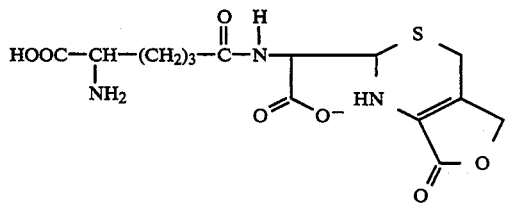

I as the sole carbon, nitrogen and energy source via the malonyl-lactone of the formula:

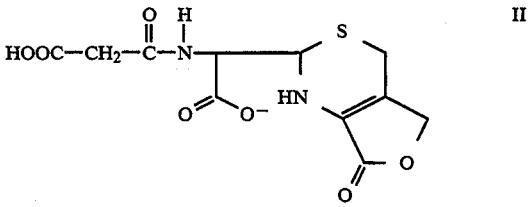

II and not catabolize the latter. These microorganisms are selected with the lactone according to formula I with the aid of traditional microbiological techniques, for example, from diverse soil samples. That is to say, if microorganisms are cultivated from soil samples as inoculum with the lactone according to formula I, microorganisms are obtained that are able to grow with the lactone as the sole carbon, nitrogen and energy source. From among these microorganisms those are then selected, according to methods usual to one skilled in the art, that convert the lactone according to formula I into the malonyl-lactone according to formula II and that do not catabolize the latter.

The lactone (of formula I) necessary for the selection can be obtained from commercially available desacetylcephalosporin C. For this purpose desacetylcephalosporin C is first lactonized to the corresponding lactone in a known way [Jeffery et al., Biochem. J., 81, (1961), pages 591 to 596]. To form the desired lactone with cleaved lactam-ring according to formula I, the lactam-ring is then cleaved by one skilled in the art, for example, by penicillinase.

In principle, all microorganisms are suitable that are obtained by this selection process. These microorganisms are not described in the literature and are a component of the invention.

Suitably the microorganisms with the designation FB1 (DSM 7007) as well as their mutants and descendants are obtained by this selection process. They were deposited on Mar. 25, 1992, with the Deutsche Sammlung für Mikroorganismen und Zellkulturen GmbH [German Collection for Microorganisms and Cell Cultures GmbH], Mascheroderweg 1b, D-3300 Brunswick, Germany. These microorganisms were identified after the Swiss priority date of this application by 16 S RNA-analysis as belonging to Sphingomonas sp.

The scientific (taxonomic) description of Sphingomonas sp. FB1 (DSM 7007) is:

| | |
|---|---|
| cell shape | tiny rods |
| width, $\mu$m | 0.4–0.6 |
| length, $\mu$m | 0.8–1.5 |
| mobility | + |
| cilia | polar 1 |
| gram reaction | − |
| lysis by 3% KOH | + |
| aminopeptidase (Cerny) | + |
| spores | − |
| oxidase | + |
| catalase | + | main quinone component: ubiquinone Q10
DNA-base composition according to HPLC quick-assay method: 63 mol % G + C.

Usually the selection and the cultivation take place in a mineral salt medium, suitably in a mineral salt medium whose composition is indicated in Table I (a and b). However, for cultivation of the microorganisms after selection has taken place, other media, such as, commercially available whole media, can also be used.

Suitably for the cultivation and selection, the lactone according to formula I is added to the mineral salt medium in an amount of 0.2 to 1 percent by weight, preferably of 0.3 to 0.6 percent by weight. The temperature during the selection and cultivation is suitably between 0° and 60° C., preferably between 20° and 40° C. The selection and cultivation are suitably performed at a pH of 5 to 9, preferably of 6 to 8. When a suitable optical density at 650 nm ($OD_{650}$) of 0.1 to 1 is reached, the microorganisms can be harvested according to methods usual to one skilled in the art and used for the process according to the invention.

According to the invention, the microorganisms in the process according to the invention selected in this way are used for the reaction of cephalosporin C derivatives of the general formula:

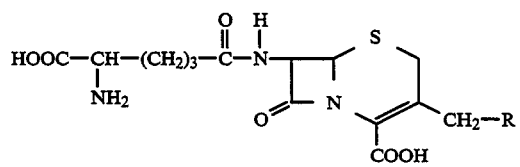

wherein R means a hydrogen atom, a hydroxyl group or an acetoxy group, as the substrate, to the malonyl-7-aminocephalosporanic acid derivatives of the general formula:

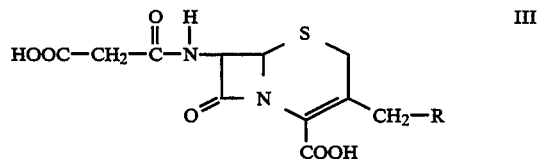

wherein R has the above-mentioned meaning. Suitably the process is performed with the selected microorganisms Sphingomonas FB1 (DSM 7007) or their descendants and mutants that are deposited as already described.

Usually the process is performed in the way usual to one skilled in the art with nongrowing cells. As the substrates, cephalosporin C derivatives of the general formula IV are used in which R has the mentioned meaning. Suitably as substrate, cephalosporin C (R in the general formula IV is an acetoxy group) is used. The substrate can be added all at once or continuously for the process. Suitably the substrate addition takes place so that the substrate concentration in the culture medium does not exceed 20 percent by weight, preferably 4 percent by weight. Media usual to one skilled in the art can be used as the media for the process. Preferably the process is performed in a low molar HEPES buffer (4-(2-hydroxyethyl)-piperazine-1-ethane-sulfonic acid). Usually the process is performed with a microorganism suspension, that has an $OD_{650}$ of 1 to 100, preferably of 2 to 50. The process is suitably performed at a temperature of 0° to 60° C., preferably of 20° to 40° C. and at a pH of 5 to 9, preferably of 6 to 8.

After a usual reaction time of 1 to 24 hours, the malonyl-7-aminocephalosporanic acid derivatives according to formula III can then be isolated in a way usual to one skilled in the art. Malonyl-7-aminocephalosporanic acid (R in the general formula III is an acetoxy group) is isolated as the preferred representative of the malonyl-7-aminocephalosporanic acid derivatives.

The process according to the invention for the production of 7-aminocephalosporanic acid derivatives of the general formula:

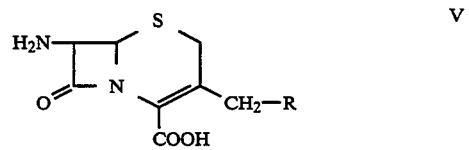

wherein R has the above-mentioned meaning, is performed so that malonyl-7-aminocephalosporanic acid derivatives or their soluble salts of the general formula III, as the substrate, are converted into the product according to formula V by microorganisms of genus Pseudomonas sp. DSM (7509) or their descendants and mutants or with cell-free enzymes from these microorganisms.

The microorganisms Pseudomonas sp. DSM 7509 were deposited on Mar. 5, 1993, with the Deutsche Sammlung für Mikroorganismen und Zellkulturen GmbH [German Collection for Microorganisms and Cell Cultures GmbH], Mascheroderweg 1b, D-3300 Brunswick, Germany. These microorganisms are known and described in Japanese Published Patent Application No. 62-48380 as microorganisms Pseudomonas sp. SE-495 (FERM BP-818). According to Japanese Published Patent Application No. 62-48380, these microorganisms are selected so that they hydrolyze glutaryl-7-aminocephalosporanic acid to 7-aminocephalosporanic acid. The use of these microorganisms for the hydrolysis of malonyl-7-aminocephalosporanic acid is not described.

Accordingly the invention also relates to the use of these microorganisms for the hydrolysis of malonyl-7-aminocephalosporanic acid derivatives (formula V), preferably of malonyl-7-aminocephalosporanic acid (R is acetoxy-). Suitably this process is performed either with microorganism cells made permeable or with a cell-free enzyme extract, especially with a cell-free enzyme extract. Methods usual to one skilled in the art, such as, treatment with ultrasound or with "French press", can be applied for the production of a cell-free enzyme extract.

Malonyl-7-aminocephalosporanic acid derivatives of the general formula V, in which R has the above-mentioned meaning, can be used as the substrate. Suitably, malonyl-7-aminocephalosporanic acid (R is acetoxy-) is used as the substrate. The substrate can be added all at once or continuously, suitably so that the substrate concentration in the culture medium does not exceed 10 percent by weight, preferably 2 percent by weight.

Any nutrient medium usual to one skilled in the art can be used as the media for this process.

If the process is performed with a cell-free enzyme extract, the protein concentration of this extract suitably is 0.1 to 20 g per l, preferably 1 to 5 g per l. Suitably the process is performed at a temperature of 4° to 50° C., preferably of 20° to 35° C. and at a pH of 4 to 9, preferably of 7 to 8.

After a usual reaction time of 3 to 24 hours, the 7-aminocephalosporanic acid derivatives according to formula V can be isolated.

Example 1
Isolation of the microorganisms

To 100 ml of mineral salt medium (Table 1), pH 7.0, containing 5 mmolar (0.5 mmol/100 ml) of the lactone with cleaved lactam ring (formula I), various soil samples from the Visp (Switzerland) area were added as inoculum and incubated at 25° C. on a shaker at 140 rpm (revolutions per minute). These cultures were inoculated 4 times to fresh mineral salt medium and then examined for this lactone reaction by analytic HPLC. These cultures were then incubated at 25° C. on mineral-salt medium agar plates containing 5 mmolar of lactone (formula I). Then the bacteria strain Sphingomonas sp. FB1 (DSM 7007), that formed the malonyl lactone of formula II during the growth from this lactone and did not completely catabolize the malonyl lactone, was isolated.

Example 2
Forming of malonyl-7-aminocephalosporanic acid (formula III)

The microorganisms Sphingomonas SP- FB1 (DSM 7007) were cultivated in a mineral salt medium, pH 7.0, (Table 1b), containing 5 mmolar of the lactone (formula I) up to an $OD_{650}$ of 0.44 within 4 days. (After the first 2 days this lactone was added again so that the total concentration was 1 mmol of lactone per 100 ml of medium.) Then the cells were centrifuged off and the cell pellet was resuspended in 20 ml of 10 mmolar HEPES buffer, pH 7.0, and adjusted to an $OD_{650}$ of 2.2. 0.4 mmol of cephalosporin C (formula IV) was added to this cell suspension. The incubation took place on the shaker (140 rpm) at 25° C. A sample of each was analyzed by HPLC analysis after 30 min., 60 min., 2.25 hr., 5.0 hr. and 24 hr. The formation rate of malonyl-7-aminocephalosporanic acid at 2.25 hr. was 410 mg/1/h/$OD_{650}$. After 5 hours, 142 mg of malonyl-7-aminocephalosporanic acid was analytically detected, which corresponded to a 99 percent reaction of cephalosporin C. The malonyl-7-aminocephalosporanic acid was able to be isolated with a yield of 40 percent by preparative HPLC.

Example 3
Identification of malonyl-7-aminocephalosporanic acid (formula III)

For identifying the product (formula III), 500 ml of mineral salt medium (Table I), pH 7.0, was mixed with a solution of the lactone of formula I so that the end concentration was 5 mmolar. Then this solution was inoculated with a preculture, whose $OD_{650}$ was 0.5, at 25° C. and 140 rpm. After one day, 5 mmol of the lactone (formula I) per 500 ml of medium was again added. When an $OD_{650}$ of 0.5 was reached, the cells were harvested. Then the cell pellet was resuspended in 30 ml of 10 mmolar HEPES buffer, pH 7.0, containing 0.6 mmol of cephalosporin C (formula IV). After a 5 hour incubation at 25° C. at 140 rpm the cells were centrifuged off and the malonyl-7-aminocephalosporanic acid was purified from the supernatant by preparative HPLC. The purified samples were freeze-dried overnight and the lyophilized culture was analyzed by NMR ($^1$H and $^{13}$C).

By comparison with a chemically produced reference substance [produced from 7-aminocephalosporanic acid according to *Bull. Soc. Chem. Belg.*, 86, (1977), pages 991–1002], the formation of malonyl-7-aminocephalosporanic acid was proven:

Malonyl-7-aminocephalosporanic acid sodium salt (chemical standard):
$^{13}$C-NMR (DMSO, 100.5 MHz, δ in ppm):
20, s; 25, s; 40, m; 58, d; 64, s; 112, s; 134, s; 164, d; 170, t.

Malonyl-7-aminocephalosporanic acid (according to the invention):
$^{13}$C-NMR (DMSO, 100.5 MHz, δ in ppm):
20, s; 25, s; 40, m; 58, d; 64, s; 112, s; 134, s; 164, d; 170, t.

Further comparison data is:
$^1$H-NMR (chem. standard, DMSO, 400 MHz, δ in ppm):
2.0,s; 2.5, s; 3.0, t; 3.5, m; 4.8, d; 5.0, d; 5.6, d.
$^1$H-NMR (according to the invention):
2.0,s; 2.5, s; 3.0, t; 3.5, m; 4.8, d; 5.0, d; 5.6, d.

Example 4
Lactonization of desacetylcephalosporin

Starting from desacetylcephalosporin C (Ciba-Geigy AG, Basel), desacetylcephalosporin C-lactone was produced as follows:

100 g of desacetylcephalosporin C was dissolved in 1120 mmolar of sodium phosphate buffer, pH 7.0. An ion exchanger [DOWEX 50X8 (Fluka) (H⁺-form)] was added to this solution until the pH reached 2.5. After 10 minutes of stirring (250 rpm, room temperature), the ion exchanger resin was filtered off and the pH of the solution was adjusted to 0.8 with concentrated hydrochloric acid. After 1 hour of stirring (room temperature, 250 rpm), DOWEX 1X8 (acetate form) (Fluka) was added to the reaction solution until a pH of 3.0 to 3.2 was attained. Then it was stirred for another 1.5 hours at 250 rpm at room temperature and then the ion exchanger resin was filtered off. Then DOWEX 1X8 (acetate form) was added again until a pH of 3.3 to 3.5 was attained, stirred for 1 hour (room temperature, 250 rpm) and then the ion exchanger resin was filtered off. The reaction solution was then evaporated to dryness (30 mbar, 30° C.) on a rotary evaporator. To remove the acetic acid that also resulted, the product was dissolved in water after concentration by evaporation until a 35 percent solution was attained and then the pH was adjusted to 1.5 with concentrated hydrochloric acid. The thus-obtained solution was extracted twice with ethyl acetate (same volume as the solution). The aqueous phases were combined and adjusted to pH 3.5 with 3 molar KOH solution and concentrated by evaporation on a rotary evaporator (30 mbar, 30° C.). The product was then dried completely in a drying oven under vacuum (30 mbar, 20° C.). The total yield was 60 g corresponding to a yield of 60 percent starting from 100 g of desacetylcephalosporin C.

Example 5
Production of lactone with cleaved lactam ring (formula I)

For the production of lactone (formula I), desacetylcephalosporin C lactone in stock solution 6 (Table 1a) was treated with a β-lactamase, penicillinase E. C. 3.5.2.6. (Sigma). The reaction started immediately after addition of the penicillinase. During the reaction the pH was held at pH 7.0 by the addition of a 1 normal NaOH solution. The reaction was ended as soon as a constant pH of 7.0 without NaOH addition was reached. After ending the reaction (about 2 hours), this solution was sterilized by filtration (0.2 μm filter) and then stored at −80° C.

Example 6

Formation of 7-aminocephalosporanic acid (formula V)

The microorganisms Pseudomonas sp. SE-495 (DSM 7509; FERM BP-818) were cultivated overnight at 30° C. in a nutrient medium (pH 7.0) containing 0.2 percent w/v of meat extract, 0.2 percent w/v of yeast extract, 0.5 percent w/v of peptone, 0.5 percent w/v of sodium glutamate and 0.005 percent w/v of magnesium sulfate. These cultures were inoculated in a fresh nutrient medium of the same composition (inoculation amount: 10 percent) and incubated 2 to 4 days. Then the cells were harvested by centrifugation (20 min. at 600 rpm), resuspended in 0.1 molar potassium phosphate buffer and recentrifuged (all of this three times each with 10 percent of the culture volume). Then the cell pellet was resuspended in the smallest possible volume with a potassium phosphate buffer and sonicated under ice cooling with ultrasound (10 times for 30 sec. each; interval 20 sec. each). From this crude extract the cell debris was then separated by centrifugation (20 min, at least, at 10,000 rpm). For the formation of 7-aminocephalosporanic acid, this crude extract (protein concentration, 2 mg/ml) was heated to room temperature and then malonyl-7-aminocephalosporanic acid in a potassium phosphate buffer was added in a concentration of 5 mmolar. All of this was incubated dormant at 25° C. and analyzed within 24 hours for the formation of 7-aminocephalosporanic acid. The analysis took place by thin-layer chromatography (plate: silica gel 60 $F_{245}$, mobile solvent: butanol-methanol-glacial acetic acid-water in a ratio of 50:30:3:17). The formation of 7-aminocephalosporanic acid (Rf-value: 0.51) starting from malonyl7-aminocephalosporanic acid (Rf-value: 0.43) was able to be detected either at a UV wave length of 254 nm or after spraying with a fluram reagent (3 mg of fluram; Fluka CH-9470 Buchs in 10 ml of acetone) at a UV wave length of 366 nm. After about 14 hours, 50 to 100 μ mole of 7-aminocephalosporanic acid was able to be detected with this crude extract containing a malonyl-7-aminocephalosporanic acid-acylase as the enzyme.

TABLE 1

| (a) Mineral salt medium stock solutions | |
|---|---|
| Stock solution 1: | |
| $NaH_2PO_4.2H_2O$ | 156.0 g |
| $NH_4Cl$ | 10.0 g |
| $K_2SO_4$ | 1.2 g |
| distilled water | 500.0 ml |
| Stock solution 2: | |
| p-aminobenzoic acid | 8.0 mg |
| D-biotin | 2.0 mg |
| nicotinic acid | 20.0 mg |
| Ca-D-pantothenate | 10.0 mg |
| pyridoxal hydrochloride | 30.0 mg |
| thiamine dichloride | 20.0 mg |
| cyanocobalamin | 10.0 mg |
| distilled water | 100.0 ml, sterilizing by filtration |
| Stock solution 3: | |
| HCl (37 percent) | 7.0 ml |
| $FeCl_2.4H_2O$ | 1.5 g |
| $ZnCl_2$ | 0.07 g |
| $MnCl_2.4H_2O$ | 0.1 g |
| $H_3BO_3$ | 0.006 g |
| $CoCl_2.6H_2O$ | 0.19 g |
| $CuCl_2.7H_2O$ | 0.002 g |
| $NiCl_2.6H_2O$ | 0.024 g |
| $Na_2MoO_4.2H_2O$ | 0.036 g |
| distilled water | 1000.0 ml, to be autoclaved, 121° C., 20 min. |

TABLE 1-continued

| Stock solution 4: | |
|---|---|
| NaOH | 0.5 g |
| $Na_2SeO_3.5H_2O$ | 0.003 g |
| $Na_2WO_4.2H_2O$ | 0.004 g |
| distilled water | 1000.0 ml, to be autoclaved, 121° C., 20 min. |
| Stock solution 5: | |
| $MgCl_2.6H_2O$ | 40.0 g |
| $CaCl_2.2H_2O$ | 5.0 g |
| distilled water | 200.0 ml, to be autoclaved, 121° C., 20 min. |
| Stock solution 6: | |
| desacetylcephalosporin C-lactone | 3.55 g |
| distilled water | 60.0 ml |
| penicillinase (EC 3.5.2.6) (Sigma p0389) | 1.0 mg (25,000 units) |
| pH to be adjusted with NaOH to | 7.0 |
| to be filled up with distilled water to | 100.0 ml |
| (b) Production of mineral salt medium | |
| stock solution 1: | 25.0 ml |
| pH to be adjusted with KOH to | 7.0 then to be filled up with distilled water to 950.0 ml, to be autoclaved, 121° C., 20 min. |
| After the sterilization addition of: | |
| stock solution 2 | 0.5 ml |
| stock solution 3 | 1.0 ml |
| stock solution 4 | 1.0 ml |
| stock solution 5 | 0.5 ml |
| solution obtained from Example 5 | 50.0 ml |

What is claimed is:

1. A microbiological process for the production of a malonyl-7-aminocephalosporanic acid derivative of formula:

$$\text{HOOC-CH}_2\text{-C(=O)-NH-}\overset{\text{S}}{\underset{\text{COOH}}{\text{[β-lactam]}}}\text{-CH}_2\text{-R} \quad \text{III}$$

wherein R is a hydrogen atom, a hydroxyl group or an acetoxy group, or a soluble salt thereof, comprising converting a cephalosporin C derivative substrate of formula:

$$\text{HOOC-CH(NH}_2\text{)-(CH}_2\text{)}_3\text{-C(=O)-NH-}\overset{\text{S}}{\underset{\text{COOH}}{\text{[β-lactam]}}}\text{-CH}_2\text{-R} \quad \text{IV}$$

wherein R is a hydrogen atom, a hydroxyl group or an acetoxy group, or a soluble salt thereof, with the microorganism Sphingomonas sp. DSM 7007 to produce the product according to the formula III.

2. A process according to claim 1 wherein the process takes place by one time or continuous addition of said substrate so that said substrate concentration in the culture medium does not exceed 20 percent by weight.

3. The process according to claim 2 wherein the process is performed at a temperature of 0° to 60° C. and a pH of 5 to 9.

4. A biologically pure culture of Sphingomonas sp. DSM 7007, or a mutant thereof capable of producing malonyl-7aminocephalosporanic acid.

* * * * *